United States Patent [19]

Bartmann et al.

[11] 4,258,057

[45] Mar. 24, 1981

[54] PROSTAGLANDIN DERIVATIVES OF THE Δ2,4-11-DEOXY-PEG SERIES

[75] Inventors: Wilhelm Bartmann, Bad Soden am Taunus; Gerhard Beck, Frankfurt am Main; Ulrich Lerch, Hofheim am Taunus; Martin Bickel, Frankfurt am Main, all of Fed. Rep. of Germany

[73] Assignee: Hoechst Aktiengesellschaft, Frankfurt am Main, Fed. Rep. of Germany

[21] Appl. No.: 54,874

[22] Filed: Jul. 5, 1979

[30] Foreign Application Priority Data

Jul. 8, 1978 [DE] Fed. Rep. of Germany ....... 2830079

[51] Int. Cl.³ ................. A01N 37/00; C07C 69/74
[52] U.S. Cl. ................. 424/305; 260/340.7; 260/340.9 P; 560/210; 560/121; 562/503; 424/317
[58] Field of Search ............ 560/121; 562/503; 424/305, 317

[56] References Cited

U.S. PATENT DOCUMENTS

| | | | |
|---|---|---|---|
| 4,061,670 | 12/1977 | Floyd, Jr. et al. ............ | 562/503 |
| 4,098,815 | 7/1978 | Babej et al. ............ | 562/503 |
| 4,165,437 | 8/1979 | Hayashi et al. ............ | 560/121 |

FOREIGN PATENT DOCUMENTS

| | | | |
|---|---|---|---|
| 2355324 | 5/1974 | Fed. Rep. of Germany ......... | 562/503 |
| 2460285 | 7/1975 | Fed. Rep. of Germany ......... | 560/121 |

OTHER PUBLICATIONS

Chem. Abstract 91:187085a.

*Primary Examiner*—Ethel G. Love
*Attorney, Agent, or Firm*—Curtis, Morris & Safford

[57] ABSTRACT

The present invention relates to novel prostaglandin derivatives of the formula I

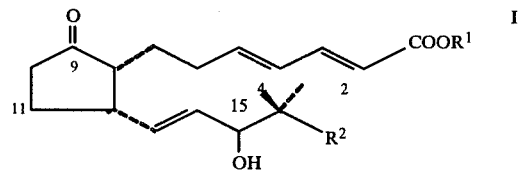

which are structurally related to the naturally occurring prostaglandins and in which $R^1$ denotes (a) hydrogen or a straight-chain or branched, saturated or unsaturated aliphatic or cycloaliphatic hydrocarbon radical having up to ten carbon atoms or (b) a physiologically acceptable metal or $NH_4$ ion or an ammonium ion which is derived from a primary, secondary or tertiary amine and $R^2$ denotes a straight-chain, aliphatic hydrocarbon radical having up to six carbon atoms and to a process for their manufacture.

The compounds of the invention are distinguished in particular by gastric acid secretion-inhibiting and ulcer-protective properties.

3 Claims, No Drawings

PROSTAGLANDIN DERIVATIVES OF THE Δ2,4-11-DEOXY-PEG SERIES

The present invention relates to novel prostaglandin derivatives of the Δ2,4-11-deoxy-PGE series.

Prostaglandins are a group of fatty acids which occur in numerous tissues and organs of humans and animals. The basic structure of the naturally occurring prostaglandins consists of 20 carbon atoms which are arranged in the form of a five-membered ring and two adjacent linear side chains (for the nomenclature see: N. Andersen, Annals of the New York Academy of Sciences, Vol. 180, Prostaglandins, page 14).

The pharmacological effects of the prostaglandins extend, inter alia, to the fields of reproduction, bronchial muscular tone, blood pressure and gastroenterology. The pharmacological properties of the naturally occurring prostaglandins are the subject of numerous review articles, for example N. H. Andersens and P. W. Ramwell in Arch, Internal. Med. 133, 30 (1974); R. L. Jones in Pathobiology Ann. 1972; J. Pike in Scient. American 225, 84 (1971) or M. P. L. Caton in Progress in Med. Chem. vol. 8. ed.: Butterworth, London, 1971.

The synthesis of prostanoic acid analogs, which are not naturally occurring and in which the multiplicity of the pharmacological effects of the naturally occurring prostaglandins are differentiated, is becoming increasingly important.

The present invention relates to novel compounds of the formula I

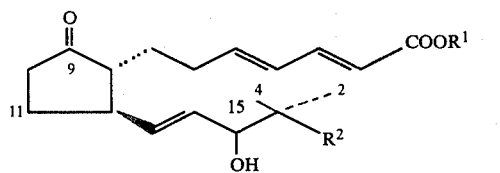

which are structurally related to the naturally occurring prostaglandins and in which $R^1$ denotes (a) hydrogen or a straight-chain or branched, saturated or unsaturated aliphatic or cycloaliphatic hydrocarbon radical having up to ten carbon atoms or (b) a physiologically acceptable metal or $NH_4$ ion or an ammonium ion which is derived from a primary, secondary or tertiary amine and $R^2$ denotes a straight-chain, aliphatic hydrocarbon radical having up to six carbon atoms.

Preferably, the present invention includes compounds of the formula I which $R^1$ denotes (a) hydrogen or a straight-chain or branched alkyl radical having up to six carbon atoms or a cycloaliphatic hydrocarbon radical having three to seven carbon atoms or (b) a physiologically acceptable metal or $NH_4$ ion or an ammonium ion which is derived from a primary, secondary or tertiary amine and $R^2$ denotes a straight-chain aliphatic hydrocarbon radical having two to six carbon atoms.

Amongst the substituents $R^1$, those listed below are particularly preferred: hydrogen, a straight-chain or branched alkyl radical having up to six carbon atoms, especially methyl, ethyl, n-propyl, n-butyl, n-pentyl, n-hexyl, iospropyl and tert.-butyl, and also cyclobutyl, cyclopentyl, cyclohexyl and cycloheptyl.

The invention also relates to a process for the manufacture of compounds of the formula I, which comprises (a) reacting an aldehyde of the formula II

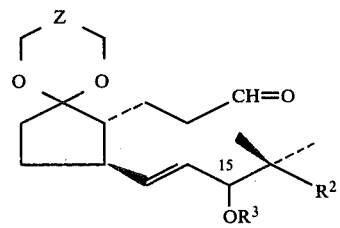

in which Z denotes a $CH_2$ group, a $—C(CH_3)_2$ group or a single bond, $R^2$ is as defined in formula I and $R^3$ represents an easily detachable protective group, with an ylide of the formula III

$$(R^4)_3P=CH—CH=CH—COOR^1 \quad \text{III}$$

in which $R^1$ is as defined under formula I but does not represent a cation and in which the substituents $R^4$ can be identical or different and denote straight-chain $(C_1-C_4)$-alkyl or phenyl, and (b) converting the resulting ester of the formula IV

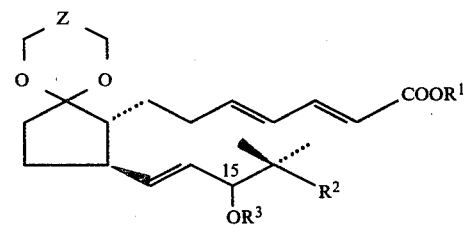

in which $R^1$ is as defined in formula III, $R^2$ is as defined in formula I and $R^3$ and Z are as defined in formula II, by acid hydrolysis to a compound of the formula I and, if desired, converting the resulting compound of the formula I in which $R^1$ is as defined in formula III and $R^2$ is as defined in formula I by treatment with bases to a compound of the formula I in which $R^1$ denotes hydrogen and $R^2$ is as defined in formula I or, if desired, esterifying a compound of the formula I in which $R^2$ is as defined in formula I and $R^1$ denotes hydrogen to a compound of the formula I in which $R^1$ and $R^2$ are as defined in formula I but $R^1$ does not denote hydrogen and, if desired, converting a compound of the formula I in which $R^2$ is as defined in formula I and $R^1$ denotes hydrogen, to a physiologically acceptable metal salt or amine salt.

The process steps for the manufacture of compounds of the formula I ($R^1$=H) can be carried out analogously to the process described in U.S. application Ser. No. 837,374 filed Sept. 28, 1977. The esterification of compounds of the formula I which are in the form of the free acids is carried out by methods which are described in U.S. application Ser. No. 809,432 filed June 23, 1977, now U.S. Pat. No. 4,198,489.

The starting materials of the formula II can be manufactured according to German Offenlegungsschrift No. 2,407,186.

The compounds, according to the invention, of the formula I are usually obtained in the form of their racemates. If desired, these can be obtained in the form of the optically active antipodes by the conventional methods for resolving racemates.

If epimer separation has not taken place at the stage of the alcohols of the general formula IV, an epimer separation of the alcohols with the functional groups in the 15-position can be carried out on the compounds of the general formula I.

In addition to those mentioned in the examples, the following compounds of the formula I, in particular, can also be manufactured: ethyl 15-hydroxy-9-oxo-16, 16-dimethyl-(E)-2,(E)-4, (E)-13-prostatrienoate, isopropyl 15-hydroxy-9-oxo-16,16-dimethyl-(E)-2,(E)-4,(E)-13prostatrienoate, 15-hydroxy-9-oxo-16,16-dimethyl-18,19,20-trinor-(E)-2, (E)-4,(E)-13-prostatrienoic acid, methyl 15-hydroxy-9-oxo-16,16-dimethyl-18,19,20-trinor-(E)-2,(E)-4, (E)-13-prostatrienoate, cyclohexyl 15-hydroxy-9-oxo-16,16-dimethyl-(E)-2, (E)-4,(E)-13-prostatrienoate, ethyl 15-hydroxy-9-oxo-16,16-dimethyl-(E)-2,(E)-4,(E)-13-prostatrienoate and ethyl 15-hydroxy-9-oxo-16,16-dimethyl-20-nor-(E)-2,(E)-4,(E)-13-prostatrienoate.

The compounds according to the invention are distinguished in particular by gastric acid secretion-inhibiting and ulcer-protective properties, as can be seen by tests carried out on rats. Thus, oral administration of from 0.03 to 1.0 mg/kg of the compound according to Example 6a inhibits, depending on the dose, both ulcer development and gastric juice secretion in rats. In the enteropooling test (increased volume of liquid in the intestines after PG administration) on rats (literature: Robert, A et al. Prostaglandins 11, (1976) No. 5, 809), the compounds according to the invention are distinguished by an advantageous quotient of the protective effective dose and the dose at which stimulation starts (enteropooling).

The compounds, according to the invention, of the formula I can be used in the form of the free acids, in the form of their physiologically acceptable inorganic and organic salts or in the form of esters.

Acids and salts or esters can be used in the form of their aqueous solutions or suspensions or as solutions or suspensions in pharmcologically acceptable organic solvents, such as monohydric or polyhydric alcohols, such as, for example, ethanol, ethylene glycol or glycerol, oils, such as, for example, sunflower oil or cod liver oil, ethers, such as, for example, diethylene glycol dimethyl ether, or polyethers, such as, for example, polyethylene glycols, or may also be used in the presence of other pharmacologically acceptable polymeric carriers, such as, for example, polyvinylpyrrolidone.

Formulations which can be used are the conventional galenic infusion or injection solutions and tablets and also formulations which can be applied locally, such as creams, emulsions, suppositories and especially aerosols.

A further application of the novel compounds lies in their combination with other active substances.

With an oral daily dose of from 0.1 to 20 mg/kg, preferably from 0.4 to 4 mg/kg, the compounds of the invention show a gastric acid secretion-inhibiting and ulcer-protective action in humans. The dosage unit considered for these indications is in the range of from 2 mg to 400 mg, preferably from 8 to 80 mg.

The compounds of the formula IV are novel valuable intermediates for the manufacture of compounds of the formula I.

The following Examples illustrate the invention.

EXAMPLE 1:

3-Carbomethoxy-2-propenyl-triphenylphosphonium bromide 111.2 g (0.425 mol) of triphenylphosphine (molecular weight 262) are dissolved in 480 ml of absolute benzene. 71.6 g (0.40 mol) of methyl γ-bromo-crotonate are added dropwise in the course of 1½ hours at room temperature, with vigorous stirring. The temperature rises to +26° C. and a white preceipitate forms. Reaction mixture is stirred at room temperature for a further 24 hours. The crystals are filtered off and washed once with benzene and 2-3 times with petroleum ether and then dried in a drying cabinet at 60° C. in vacuo.

Yield: 139.9 g; melting point: crude 175°C. (decomposition product)

$[C_{23}H_{22}O_2P]$ Br (441.2): Calculated: C,62.6; H,5.03; P,7.02; Br, 18.11. Found: C,62.65; H,5.2; P,7.2; Br, 18.0.

EXAMPLE 2:

[3-Carbomethoxy-2-propene-1-ylidene]-triphenyl-phosphorane III 66.15 g (0.15 mol) of 3-carbomethoxy-2-propenyltriphenylphosphonium bromide were dissolved in 3.5 l of cold $H_2O$. 6 g (0.15 mol) of NaOH were then dissolved in 300 ml of $H_2O$ and this solution was added dropwise in the course of 1½ hours forming a yellow-orange precipitate.

The precipitate was then filtered off immediately and washed well with $H_2O$. The product was placed on a clay plate and pre-dired over KOH in vacuo in a desiccator for 2 days, then dired completely over $P_2O_5$. The product is stored in valuo with $P_2O_5$ in a desiccator.

Yield: 39.5 g (III) Melting point: 166° C. (sintering above 160° C.)

NMR: $\delta$=3.6 (s,3) COOCH$_3$; 7.1-8.0 (m, 16) C$_6$H$_5$—, (CDCL$_3$) —CH=P 5.2(d,l)C$\underline{H}$=, 3.65(d,l)CH=C$\underline{H}$—COOCH$_3$

EXAMPLE 3a

3-[7-(4,4-Dimethyl-3-tetrahydro-pyranyloxy-(E)-1-octen-1-yl)-1,4-dioxaspiro[4.4]non-6-yl]-propionaldehyde II (Z = CH$_2$, R$^2$ = n-C$_4$H$_9$, R$^3$ = 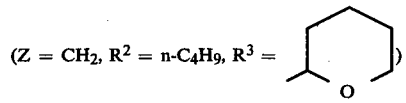)

prepared analogously to Example 14a–14d of the process described in German Offenlegungsschrift 2,407,186.

The product was a yellow oil which was not further purified. In its infra-red spectrum, compound II has a strong carbonyl band at 1,730 cm−1 Thin layer chromatography: R$_f$ value 0.53 on silica gel plates from Messrs. Merck in cyclohexane/ethyl acetate, 1:1 NMR: $\delta$0.9(d,6) C(CH$_3$)$_2$; 0.9 (t,3)—CH$_3$; 1.1–1.4(6)CH$_2$ (CDCl$_3$) (THP);

1.4–2.7 (m,16) C$\underline{H}_2$-, C$\underline{H}$; 3.2–4.0 (m,3) C$\underline{H}_2$O, C$\underline{H}$—O—THP;

3.9 (s,4) CH$_2$O; 4.5–4.7 (M,2) —O—C$\underline{H}$—O—;

5.2–5.6 (m,2) CH=CH, 9.65 (s,1) CH=O

EXAMPLE 3b

3-[7-(4,4-Dimethyl-3-tetrahydropyranyloxy-(E)-1-nonen-1-yl)-1,4-dioxaspiro[4.4]non-6-yl]-propionaldehyde II (Z = CH$_2$, R$^2$ = n-C$_5$H$_{11}$, R$^3$ = 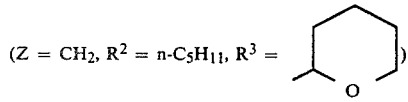)

prepared analogously to Example 3a.

NMR: δ 0.9 (d,6) C(CH$_3$)$_2$; 0.9 (t,3)CH$_3$; 1.1–1.4 (CDCl$_3$) (6) C$\underline{H}_2$ (THP);
1.4–2.65 (m,18) C$\underline{H}_2$-, C$\underline{H}$; 3.2–4.0 (m,3) CH$_2$O, C$\underline{H}$—O—THP;
3.9 (s,4) CH$_2$O; 4.5–4.7 (m,2)—O—C$\underline{H}$—O—;
5.2–5.6 (m,2) CH=CH, 9.6 (s,1) CH=O

EXAMPLE 3c:

3-[7-(4,4-Dimethyl-3-tetrahydropyranyloxy-(E)-1-hepten-1-yl)-1,4-dioxaspiro[4.4]non-6yl]-propionaldehyde II (Z = CH$_2$, R$^2$ = n-C$_3$H$_7$, R$^3$ = 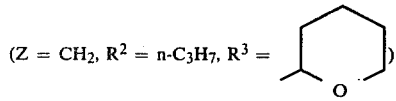)

prepared analogously to Example 3a.

NMR: δ 0.9 (d,6) C(CH$_3$)$_2$; 0.9 (t,3) CH$_3$; 1.1–1.45 (6) (CDCL$_3$) C$\underline{H}_2$ (THP);
1.35–2.6 (m,14) C$\underline{H}_2$—, C$\underline{H}$; 3.2–4.05 (m,3) CH$_2$O, C$\underline{H}$—O—THP;
3.95 (s,4) CH$_2$O; 4.5–4.65 (m,2) —O—C$\underline{H}$—O;
5.1–5.7 (m,2) CH=CH, 9.5 (s,1) CH=O

EXAMPLE 4a:

Methyl 7-[7-(4,4-dimethyl-3-tetrahydropyranyloxy-(E)-1-octen-1-yl)-1,4-dioxaspiro[4.4]non-6-yl]-(E)-2,(E)-4-heptadienoate IV (Z = CH$_2$, R$^1$ = CH$_3$, R$^2$ = n-C$_4$H$_9$, R$^3$ = 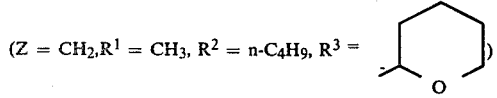)

5.77 g (0.0136 mol) of 3-[7(4,4-dimethyl-3-tetrahydropyranyloxy-(E)-1-octen-1-yl)-1,4-dioxaspiro[4.4]-non-6-yl]-propionaldehyde (Example 3a) are dissolved in 120 ml of absolute benzene (argon as blanketing gas). 14.74 g (0.0408 mol) of [3-carbomethoxy-2-propen-1-ylidene]-triphenyl-phosphorane (Example 2) are added dropwise to this solution, with the exclusion of moisture, and the reaction mixture is then warmed under reflux for 2½ hours. The batch is then concentrated in vacuo, the residue is extracted with ether and the ethereal extracts are again concentrated in vacuo. A yellow oil remains and this is chromatographed on silica gel using ether as the eluant. Yield: 6.21 g of a pale yellow oil (IV)

NMR: δ 0.9 (d,6) C(CH$_3$)$_2$; 0.9 (t,3) CH$_3$; 1.1–1.4 (6) (CDCl$_3$) C$\underline{H}_2$ (THP);
1.4–2.7 (m,16) C$\underline{H}_2$, C$\underline{H}$; 3.7 (s,3) COOC$\underline{H}_3$, 3.9 (s,4) C$\underline{H}_2$O 3.1–4.0 (m,3) CH$_2$O, C$\underline{H}$-OTHP; 4.5–4.65 (m,2) O—CH—O;
5.0–6.8 (m,6) olefinic protons.

EXAMPLE 4b:

Methyl 7-[7-(4,4-dimethyl-3-tetrahydropyranyloxy-(E)-1-nonen-1-yl)-1,4-dioxaspiro[4.4]non-6-yl]-(E)-2,(E)-4-heptadienoate IV (Z = CH$_2$, R$^1$ = CH$_3$, R$^2$ = n-C$_5$H$_{11}$, R$^3$ = 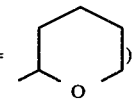)

Reaction analogous to Example 4a from 3-[7-(4,4-dimethyl-3-tetrahydropyranyloxy-(E)-1-nonen-1-yl)-1,4-dioxaspiro[4.4]non-6-yl]-propionaldehyde NMR: δ 0.9 (d,6) C(CH$_3$)$_2$; 0.9 (t,3) CH$_3$; 1.1–1.4 (6) (CDCl$_3$) C$\underline{H}_2$ (THP);
1.4–2.65 (m,18) C$\underline{H}_2$, C$\underline{H}$; 3.75 (s,3) COOCH$_3$; 3.9 (s,4) (C$\underline{H}_2$O;
3.1–4.0 (m,3) CH$_2$O,C$\underline{H}$-OTHP; 4.5–4.65 (m,2) O—CH—O; 5.0–6.65 (m,6) olefinic protons.

EXAMPLE 4c:

Methyl 7-[7-(4,4-dimethyl-3-tetrahydropyranyloxy-(E)-1-hepten-1-yl)-1,4-dioxaspiro[4.4]non-6-yl]-(E)-2,(E)-4-heptadienoate IV (Z = CH$_2$, R$^1$ = CH$_3$, R$^2$ = n-C$_3$H$_7$, R$^3$ = 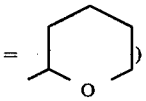)

Reaction analogous to Example 4 a from 3-[7-(4,4-dimethyl-3-tetrahydropyranyloxy-(E)-1-hepten-1-yl)-1,4-dioxaspiro[4.4]non-6-yl]-propionaldehyde NMR: δ 0.9 (d,6) C(CH$_3$)$_2$; 0.9 (t,3) CH$_3$; 1.1–1.4 (6) (CDCl$_3$) C$\underline{H}_2$ (THP);
1.4–2.6 (m,14) C$\underline{H}_2$, C$\underline{H}$; 3.75 (s,3) COOCH$_3$; 3.9 (s,4) CH$_2$O;
3.1–4.1 (m,3) C$\underline{H}_2$O, C$\underline{H}$—O—THP; 4.5–4.65 (m,2) O—CH—O;
5.1–6.7 (m,6) olefinic protons

EXAMPLE 5 a:

Methyl 7-[5-oxo-2-(3-hydroxy-4,4-dimethyl-(E)-1-octen-1-yl)-cyclopentan-1-yl]-(E)-2,(E)-4-heptadienoate I (R$^1$=CH$_3$, R$^2$=n-C$_4$H$_9$)

6.12 g of methyl 7-[7-(4,4-dimethyl-3-tetrahydropyranyloxy-(E)-1-octen-1-yl)-1,4-dioxaspiro[4.4]-non-6-yl]-(E)-2,(E)-4-heptadienoate (Example 4a) are dissolved in 200 ml of methanol. 30 ml of cold, saturated aqueous oxalic acid solution are added to this solution and the mixture is stirred for 2 days at room temperature. The solvent is then removed in vacuo, saturated sodium chloride solution is added to the residue and the mixture is then extracted with ether. The ether phase is washed with water until neutral, dried over MgSO$_4$ and concentrated in vacuo.

Yield: 4.4 g of a yellow oil

Thin layer chromatography:

R$_f$=0.43 15β-epimer
R$_f$=0.36 15α-epimer on silica gel plates from Messrs. Merck in cyclohexane/ethyl acetate=1:1

EXAMPLE 5 b:
Methyl 7-[5-oxo-2-(3-hydroxyl-4,4-dimethyl-(E)-1-nonten-1-yl)-cyclopentan-1-yl]-(E)-2,(E)-4-heptadienoate I ($R^1 = CH_3$, $R^2 = n\text{-}C_5H_{11}$)

Reaction analogous to Example 5 a from methyl 7-[7-(4,4-dimethyl-3-tetrahydropyranyloxy-(E)-1-nonen-1-yl)-1,4-dioxaspiro[4.4]non-6-yl]-(E)-2,(E)-4-heptadienoate. Thin layer chromatography:
$R_f = 0.42$ 15β-epimer
$R_f = 0.37$ 15α-epimer
on silica gel plates from Messrs. Merck, in cyclohexane/ethyl acetate = 1:1.

EXAMPLE 5 c:
Methyl 7-[5-oxo-2-(3-hydroxy-4,4-dimethyl-(E)-1-hepten-1-yl)-cyclopentan-1-yl]-(E)-2,(E)-4-heptadienoate I ($R^1 = CH_3$, $R^2 = n\text{-}C_3H_7$)

Reaction analogous to Example 5 a from methyl 7-[7-(4,4-dimethyl-3-tetrahydropyranyloxy-(E)-1-hepten-1-yl)-1,4-dioxaspiro[4.4]non-6-yl]-(E)-2,(E)-4-heptadienoate.
Thin layer chromatography:
$R_f = 0.44$ 15β-epimer
$R_f = 0.38$ 15α-epimer
on silica gel plates from Messrs. Merck, in cyclohexane/ethyl acetate = 1:1.

EXAMPLE 6 a:
7-[5-Oxo-2-(3-hydroxy-4,4-dimethyl-(E)-1-octen-1-yl)-cyclopentan-1-yl]-(E)-2,(E)-4-heptadienoic acid I ($R^1 = H$, $R^2 = n\text{-}C_4H_9$)

4.4 g of methyl 7-[5-oxo-2-(3hydroxy-4,4-dimethyl-(E)-1-octen-1-yl)-cyclopentan-1-yl]-(E)-2,(E)-4-heptadienoate are dissolved in 10 ml of methanol. 23.4 ml of 1 M NaOH (twofold excess) are added to this solution and the mixture is stirred for 48 hours at room temperature. the course of reaction was followed in a thin layer chromatogram. 30 g of ice and solid sodium chloride are then added and the mixture is acidified to pH 1–2 with 2 N hydrochloric acid. The aqueous phase is extracted with ether, the ether phase is then washed with water until neutral, dried over $MgSO_4$ and concentrated in vacuo and the residue is chromatographed on silica gel. Eluant: cyclohexane/ethyl acetate/glacial acetic acid = 40/60/1
Yield: 3.2 g of a yellow oil
Thin layer chromatography:
$R_f = 0.35$ 15β-epimer
$R_f = 0.31$ 15α-epimer
(Silica gel plates from Messrs. Merck, in cyclohexane/ethyl acetate/glacial acetic acid, 40/60/1)
NMR: δ0.9 (s,6) $C(CH_3)_2$; 1.1–2.8 (m,16) —$CH_2$—, —CH—; ($CDCl_3$) 3.25–3.4 (m,1) —C$\underline{H}$∼OH; 3.6–4.6 (broad signal, 2) COO$\underline{H}$, O$\underline{H}$;
5.5–6.3 (m,6) olefinic protons.

EXAMPLE 6 b:
7-[5-Oxo-2-(3-hydroxy-4,4-dimethyl-(E)-1-nonen-1-yl)-cyclopentan-1-yl]-(E)-2,(E)-4-heptadienoic acid I ($R^1 = H$, $R^2 = n\text{-}C_5H_{11}$)

Reaction analogous to Example 5 a from methyl 7-[5-oxo-2-(3-hydroxy-4,4-dimethyl-(E)-1-nonen-1-yl)-cyclopentan-1-yl]-(E)-2,(E)-4-heptadienoate.
Thin layer chromatography:
$R_f = 0.34$ 15β-epimer
$R_f = 0.30$ 15α-epimer
Silica gel plates from Messrs. Merck, in cyclohexane/ethyl acetate/glacial acetic acid, 40/60/1.
NMR δ0.9 (s,6) $C(CH_3)_2$; 1.1–2.7 (m,18) —$CH_2$, —CH—; ($CDCl_3$) 3.2–3.4 (m,1—C$\underline{H}$—OH; 3.2–4.2 (broad signal, 2)
COO$\underline{H}$, O$\underline{H}$;
5.5–6.2 (m,6) olefinic protons.

EXAMPLE 6 c:
7-[5-Oxo-2-(3-hydroxy-4,4-dimethyl-(E)-1-hepten-1-yl)-cyclopentan-1-yl]-(E)-2,(E)-4-heptadienoic acid I ($R^1 = H$, $R^2 = n\text{-}C_3H_7$)

Reaction analogous to Example 5 a, from ethyl 7-[5-oxo-2-(3-hydroxy-4,4-dimethyl-(E)-1-hepten-1-yl)-cyclopentan-1-yl]-(E)-2,(E)-4-heptadienoate.
Thin layer chromatography:
$R_f = 0.36$ 15β-epimer
$R_f = 9.32$ 15α-epimer
Silica gel plates from Messrs. Merck, in cyclohexane/ethyl acetate/glacial acetic acid, 40/60/1.
NMR: δ0.9 (s,6) $C(CH_3)_2$; 1.1–2.9 (m,14) —$CH_2$, —CH—; ($CDCl_3$) 3.2–3.4 (m,1)—CH∼OH; 3.4–4.6 (broad signal, 2)
COOH, OH;
5.5–6.2 (m,6) olefinic protons.

EXAMPLE 7a:
Sodium salt of 7-[5-oxo-2-(3-hydroxy-4,4-dimethyl-(E)-1-octen-1-yl)-cyclopentan-1-yl]-(E)-2,(E)-4-heptadienoic acid I ($R^1 = Na$, $R^2 = n\text{-}C_4H_9$)

362.5 mg of 7-[5-oxo-2-(3-hydroxy-4,4dimethyl-(E)-1-octen-1-yl)-cyclopentan-1-yl]-(E)-4-heptadienoic acid are dissolved in 4 ml of ethanol and 5 ml of a 0.2 molar solution of sodium hydroxide in ethanol are added. By evaporating the solvent, the sodium salt is obtained as a viscous oil.

EXAMPLE 7b:
Tromethamine salt of 7-[5-oxo-2-(3-hydroxy-4,4-dimethyl-(E)-1-nonen-1-yl)-cyclopenten-1-yl]-(E)-2,(E)-4-heptadienoic acid I ($R^1 = H_3N^\oplus$—$C(CH_2OH)_3$, $R^2 = n\text{-}C_5H_{11}$)

An ethanolic solution of 60.6 mg of tromethamine is added to a solution of 188.25 mg of 7-[5-oxo-2-(3-hydroxy-4,4-dimethyl-(E)-1-nonen-1-yl)-cyclopenten-1-yl]-(E)-2,(E)-4-heptadienoic acid in 4 ml of ethanol and the solvent is evaporated, finally under a high vacuum.

EXAMPLE 8:
Ethyl 7-[5-oxo-2-(3-hydroxy-4,4-dimethyl-(E)-1-hepten-1-yl)-cyclopentan-1-yl]-(E)-2,(E)-4-heptadienoate I ($R^1 = C_2H_5$, $R^2 = n\text{-}C_3H_7$)

5 ml of a 1 M solution of diazoethane in ether are added to a solution of 350.5 mg of 7-[5-oxo-2-(3-hydroxy-4,4-dimethyl-(E)-1-hepten-1-yl)-cyclopentan-1-yl]-(E)-2,(E)-4-heptadienoic acid in 6 ml of ether, with ice-cooling. The mixture is then stirred for a further 30 minutes and the solvent is evaporated with the excess diazoethane in vacuo. The product is pure according to chromatography. NMR: 1.25 (t,3) —COO$CH_2$$CH_3$; 4.25 (q,2) —COOC$\underline{H}_2$$CH_3$ ($CDCl_3$) 5.5–6.2 (m,6) olefinic protons.

What is claimed is:
1. A compound of the formula

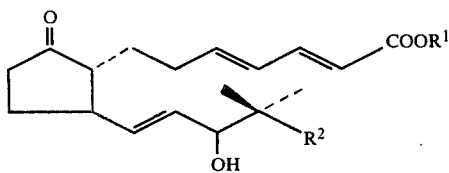

wherein $R^2$ is straight-chain aliphatic hydrocarbon having up to 6 carbon atoms and $R^1$ is hydrogen, straight-chain or branched, saturated or unsaturated aliphatic or cycloaliphatic hydrocarbon having up to 10 carbon atoms, a physiologically acceptable metal ion, $NH_4+$, or an ammonium ion derived from a primary, secondary, or tertiary amine.

2. A pharmaceutical composition for the treatment of inflammatory and ulcerative gastrointestinal muscosal changes, which composition comprises an anti-inflammatory and anti-ulcerative effective amount of a compound as in claim 1 and a pharmaceutically acceptable carrier and/or stabilizer therefor.

3. A method for the treatment of inflammatory and ulcerative gastrointestinal mucosal changes, which method comprises administering an anti-inflammatory and anti-ulcerative effective amount of a compound as in claim 1.

* * * * *